United States Patent [19]
Love

[11] Patent Number: 5,297,564
[45] Date of Patent: Mar. 29, 1994

[54] CATHETER TECHNIQUE FOR CREATION OF AN AORTICO-PULMONARY SHUNT

[76] Inventor: Jack W. Love, 785 Corosam Rd., Santa Barbara, Calif. 93110

[21] Appl. No.: 936,767

[22] Filed: Aug. 27, 1992

[51] Int. Cl.⁵ .......................................... A61B 19/00
[52] U.S. Cl. .............................. 128/898; 128/662.03; 606/14; 623/2
[58] Field of Search ................ 606/7, 13, 14–16; 128/898, 662.03, 662.05, 662.06; 606/108; 623/2-3

[56] References Cited

U.S. PATENT DOCUMENTS

| | | |
|---|---|---|
| 4,785,806 | 11/1988 | Deckelbaum ............ 606/7 |
| 4,791,926 | 12/1988 | Fry ......................... 606/7 |
| 4,807,596 | 2/1989 | Hochberger et al. ...... 606/14 |
| 4,832,024 | 5/1989 | Boussignac et al. ...... 606/7 |
| 4,860,743 | 8/1989 | Abela ...................... 606/7 |
| 4,862,886 | 9/1989 | Clarke et al. ............ 606/15 |
| 4,862,887 | 9/1989 | Weber et al. ............. 606/7 |
| 4,905,689 | 3/1990 | Stack et al. .............. 606/15 |
| 5,109,859 | 5/1992 | Jenkins ..................... 606/7 |
| 5,125,058 | 6/1992 | Tenerz et al. ............. 606/16 |
| 5,151,098 | 9/1992 | Loertscher ................ 606/16 |
| 5,158,560 | 10/1992 | Sogawa et al. ........... 606/15 |
| 5,166,990 | 11/1992 | Riccitelli et al. ......... 606/15 |

Primary Examiner—Randall L. Green
Assistant Examiner—Gina M. Gualtieri
Attorney, Agent, or Firm—Knobbe, Martens, Olson & Bear

[57] ABSTRACT

A method of creating an aortico-pulmonary shunt with a catheter is provided.

11 Claims, 2 Drawing Sheets

CATHETER TECHNIQUE FOR CREATION OF AN AORTICO-PULMONARY SHUNT

BACKGROUND OF THE INVENTION

1. Field of the Invention

This invention relates generally to a surgical method for creation of an aortico-pulmonary shunt, and, more specifically, to a method which utilizes a catheter to create the shunt.

2. Background of the Invention

Congenital heart defects, which can cause obstruction of pulmonary blood flow and right-to-left shunting of blood result in a condition known as cyanosis, which manifests itself in infants in what is commonly known as the "blue baby" syndrome. The commonest such condition is the Tetralogy of Fallot, which appears is approximately two of each 10,000 live births, is one of the three most common forms of congenital heart disease necessitating what is typically surgical correction in the first year of life, and accounts for 10% of patients seen in larger pediatric cardiology clinics. Of those cyanotic patients over two years of age who have not yet required or received surgery, about 75% have the Tetralogy of Fallot. Additional background on the incidence of this condition is available in "Congenital Heart Disease in 56,109 Births—Incidence and National History," Mitchell et al, Circulation, Vol XLIII, March 1971, pp. 323-332, which is hereby fully incorporated by reference herein as though set forth in full Conventional methods for treating this condition involve the surgical creation of a communication between the aortic and pulmonary circulations with the objective of increasing pulmonary blood flow, improved oxygenation, and relief of cyanosis. The first such procedure, known as the Blalock-Tarissig Shunt, involved creation of a shunt by anastomosing the proximal end of the divided subclavian artery to the left or right pulmonary artery.

These conventional methods all suffer from the disadvantage that they involve a major surgical procedure on a sick child. A second disadvantage is that all suffer from a lack of controllability of the size of the shunt, which is problematic, since a shunt which is too large may result in heart failure in the child, while a shunt which is too small will result in the child not achieving maximum benefit. A third disadvantage is the difficulty of increasing the size of the shunt as the child grows, and the difficulty of closing the shunt at the time of a surgical "total correction" of the congenital heart defect.

Accordingly, it is an object of the subject invention to provide a method of creating an aortico-pulmonary shunt which overcomes the disadvantages of prior art methods. Additional objects and advantages will be set forth in the description which follows or will be apparent to those of ordinary skill in the art who practice the invention.

SUMMARY OF THE INVENTION

To achieve the foregoing objects, and in accordance with the purpose of the invention as embodied and broadly described herein, there is provided a method for creating an aortico-pulmonary shunt, comprising the steps of:

(a) introducing a catheter into the body;

(b) positioning the catheter within a blood vessel to a location where the pulmonary artery and aorta form a common trunk;

(c) utilizing a laser to form a hole between the aorta and pulmonary artery at the location along the common trunk through ablation;

(d) utilizing the catheter to monitor hemodynamics and oxygenation; and (e) optionally utilizing the laser to increase the size of the hole until the monitored characteristics achieve a predetermined level.

DESCRIPTION OF THE PREFERRED EMBODIMENTS

Figure 1:
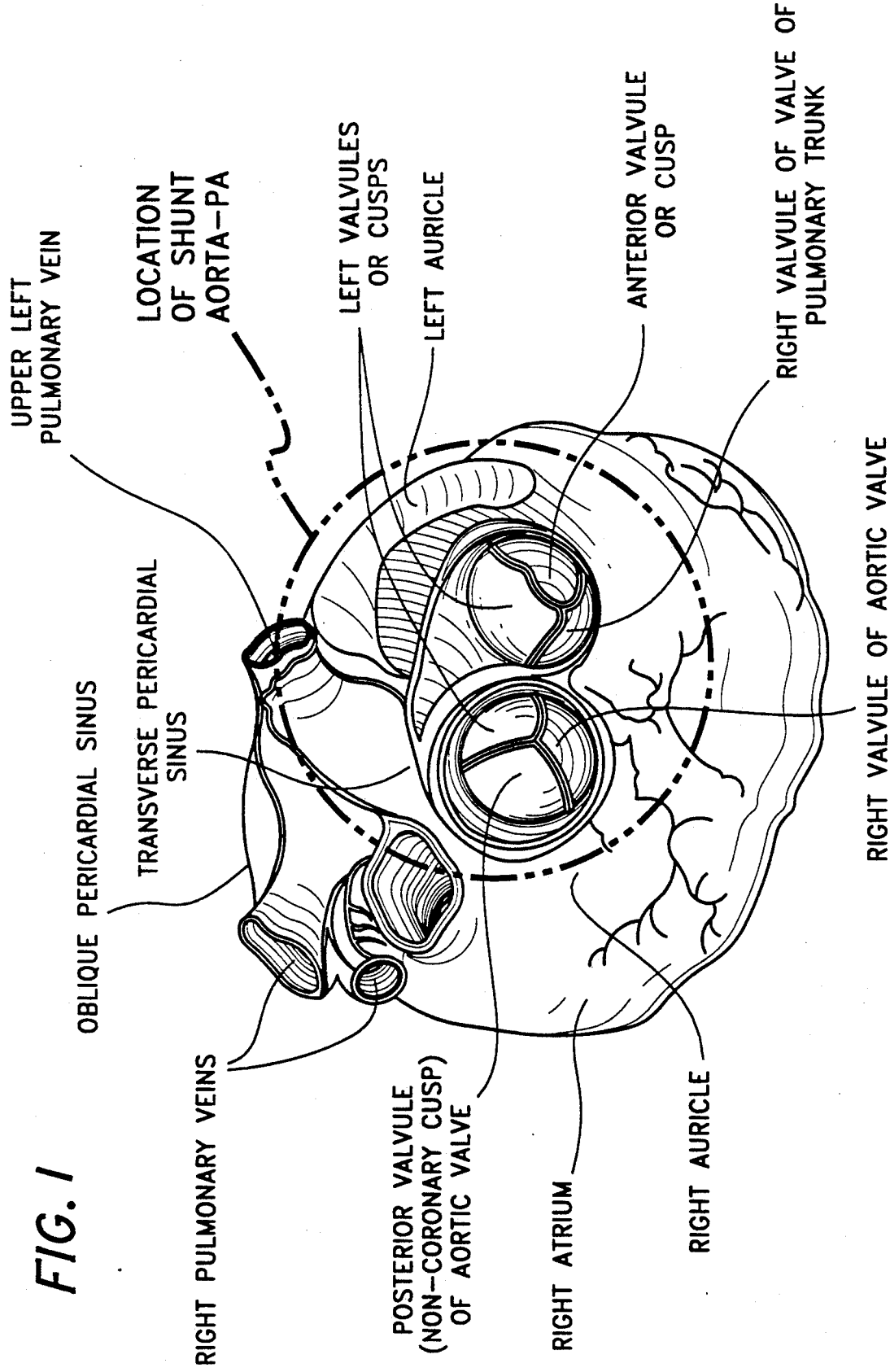
FIG. 1 is a top view of a heart, showing the best location for creation of an aortico-pulmonary shunt.
Figure 2:
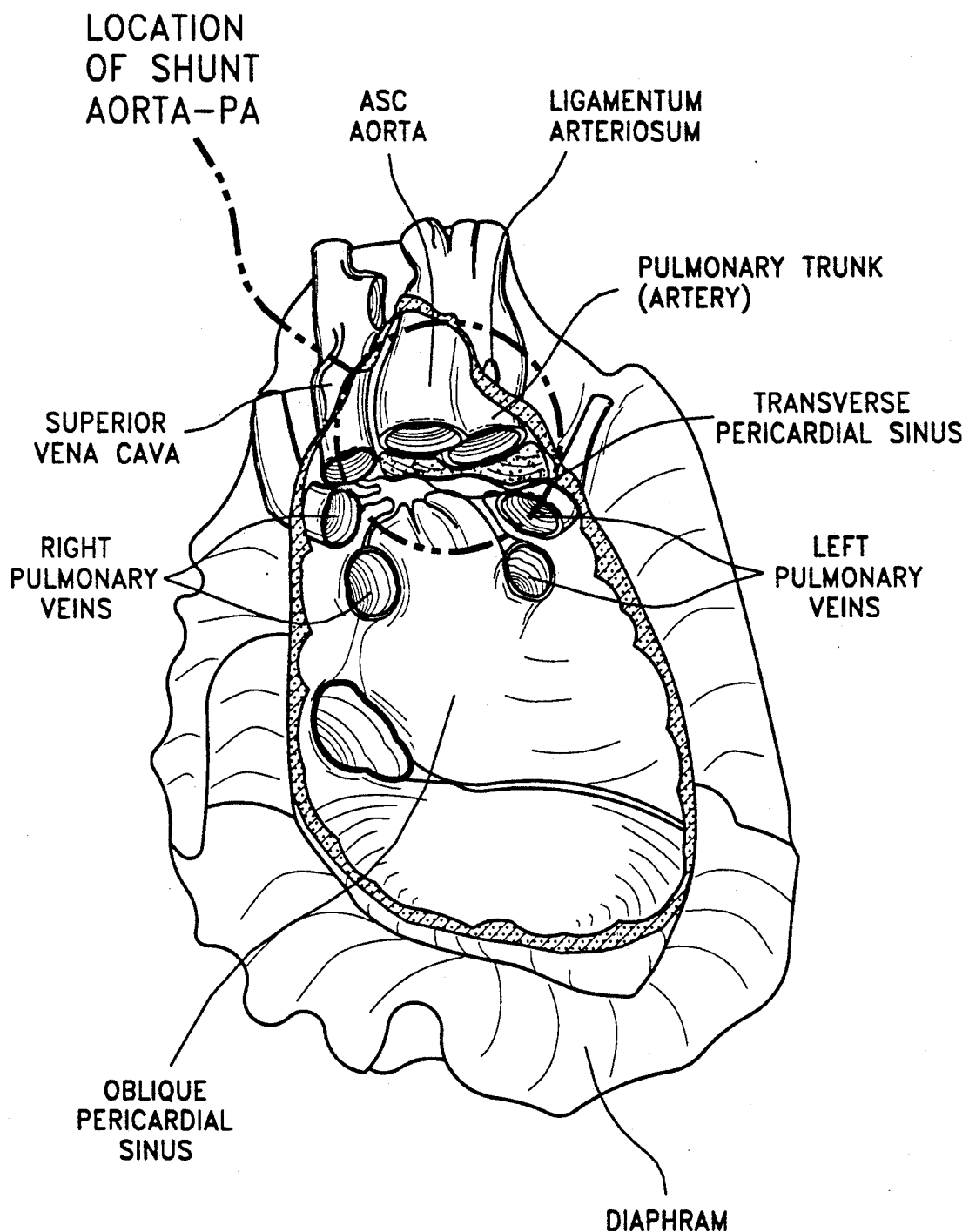
FIG. 2 is an anterior view of the heart, again showing the best location for creation of an aortico-pulmonary shunt.

The method of the subject invention begins when a catheter is inserted into a blood vessel at an appropriate location on the body, advantageously, the upper thigh, and then positioned using ultrasonic imaging to a point where the aorta forms a common trunk with the pulmonary artery. FIG. 1 is a top view of the heart where this area is circled, and FIG. 2 is an anterior view of the heart where this area is again circled. (Alternatively, the catheter could be positioned using a fine needle to produce and establish the correct position.)

Next, a laser, such as an excimer laser, is utilized in conjunction with the catheter to form a small hole in the common trunk. The laser removes tissue through the process of ablation. The laser is turned on at a level and duration determined appropriate to create a path of communication between the aorta and pulmonary artery.

The catheter can be coupled to equipment determined appropriate to measure a characteristic such as blood flow, blood pressure, oxygen saturation, and the like. The size of the communication is preferably made small at first, and then increased in size during the procedure until the monitored characteristic achieves a predetermined level.

The use of a catheter in this method is advantageous since it eliminates the need for a major surgical procedure to create the shunt. Moreover, controllability of the shunt size is obtained by creating only a small hole at first and then incrementally increasing the size of the hole responsive to a monitored characteristic of the body. The difficulty of increasing the size of the shunt as the child grows is also avoided since subsequent catheterization procedures can be performed simply and inexpensively, without significant trauma to the child. Finally, if the child becomes a candidate for a surgical "total correction" of the congenital heart defect, the shunt can be closed more easily than with conventional surgical techniques.

While embodiments and applications of this invention have been shown and described, it should be apparent to those skilled in the art that many more embodiments are possible without departing from the spirit and scope of the subject invention. Accordingly, the invention is not to be restricted, except as by the appended claims.

What is claimed is:

1. A method for creating an aortico-pulmonary shunt in the human body at the location of the chambers of the heart where the pulmonary artery and aorta form a common trunk, comprising the steps of:
   (a) introducing a catheter into the body, said catheter being coupled to equipment for monitoring blood and oxygen characteristics;
   (b) positioning the catheter within a blood vessel to said location outside the chambers of the heart where the pulmonary artery and aorta form a common trunk;
   (c) utilizing a laser to form a hole through said common trunk between the aorta and pulmonary artery at said location along a common trunk through the process of ablation;
   (d) utilizing the catheter to monitor a characteristic of the body; and
   (e) optionally utilizing the laser to increase the size of the hole until the monitored characteristic achieves a predetermined level.

2. The method of claim 1 wherein step (b) comprises positioning the catheter within the pulmonary artery.

3. The method of claim 1 wherein step (b) comprise positioning the catheter within the aorta.

4. The method of claim 1 wherein step (c) comprises utilizing an excimer laser.

5. The method of claim 1 wherein step (d) comprises monitoring blood flow.

6. The method of claim 1 wherein step (d) comprises monitoring blood pressure.

7. The method of claim 1 wherein step (d) comprises monitoring oxygen saturation.

8. The method of claim 1 wherein step (b) comprises positioning the catheter using ultrasonic imaging.

9. The method of claim 1 wherein step (b) comprises positioning the catheter using a fine needle.

10. A method for creating an aortico-pulmonary shunt in the human body at a location outside of the chambers of the heart where the pulmonary artery and aorta form a common trunk without performing a surgical procedure at the situs of said shunt, comprising the steps of:
    (a) introducing a catheter into the body, said catheter being coupled to equipment for monitoring blood and oxygen characteristics;
    (b) utilizing ultrasonic imaging to position said catheter outside of the chambers of the heart at said location where the pulmonary artery and aorta form a common trunk;
    (c) utilizing a laser in conjunction with said catheter to remove tissue through the process of ablation to form a hole through said common trunk so that the aorta and pulmonary artery are in communication at said location along said common trunk;
    (d) monitoring the blood and oxygen characteristics; and
    (e) utilizing the laser to increase the size of the hole until the monitored characteristic achieves a predetermined level.

11. A method for creating an aortico-pulmonary shunt in the human body at a location outside of the chambers of the heart where the pulmonary artery and aorta form a common trunk without performing a surgical procedure at the situs of said shunt, comprising the steps of:
    (a) introducing a catheter into the body, said catheter being coupled to equipment for monitoring blood and oxygen characteristics;
    (b) utilizing ultrasonic imaging to position said catheter outside of the chambers of the heart at said location where the pulmonary artery and aorta form a common trunk; and
    (c) utilizing a laser in conjunction with said catheter to remove tissue through the process of ablation to form a hole through said common trunk so that the aorta and pulmonary artery are in communication at said location along said common trunk.

* * * * *

UNITED STATES PATENT AND TRADEMARK OFFICE
CERTIFICATE OF CORRECTION

PATENT NO. : 5,297,564

DATED : March 29, 1994

INVENTOR(S) : Love

It is certified that error appears in the above-identified patent and that said Letters Patent is hereby corrected as shown below:

In Column 3, line 2 replace "location of the chambers" with --location outside of the chambers--.

Signed and Sealed this

Twenty-sixth Day of May, 1998

Attest:

Attesting Officer

BRUCE LEHMAN

Commissioner of Patents and Trademarks